(12) United States Patent
Walter

(10) Patent No.: US 9,717,814 B2
(45) Date of Patent: Aug. 1, 2017

(54) DISPENSING DEVICE

(75) Inventor: Scott D. Walter, Twin Lakes, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 1132 days.

(21) Appl. No.: 12/896,583

(22) Filed: Oct. 1, 2010

(65) Prior Publication Data

US 2012/0080537 A1  Apr. 5, 2012

(51) Int. Cl.
*A61L 9/02* (2006.01)
*A61L 9/12* (2006.01)
*A61L 9/14* (2006.01)
*B65D 75/32* (2006.01)
*A61L 9/03* (2006.01)

(52) U.S. Cl.
CPC ............. *A61L 9/12* (2013.01); *B65D 75/326* (2013.01); *A61L 9/03* (2013.01); *A61L 2209/131* (2013.01); *A61L 2209/133* (2013.01); *A61L 2209/15* (2013.01); *B65D 2313/04* (2013.01)

(58) Field of Classification Search
CPC ......... A61H 33/12; A61H 33/06; A24F 25/00; A61L 9/04; A61L 9/00; A61L 9/02; A61L 9/03; A61L 9/12; A61L 9/14; A01G 13/06; F22B 29/06; F22B 1/28
USPC ............................. 392/386–406; 239/34–60
See application file for complete search history.

(56) References Cited

U.S. PATENT DOCUMENTS

| | | |
|---|---|---|
| 2,742,090 A | 4/1956 | Garrison |
| 2,931,880 A | 4/1960 | Yaffe |
| 2,942,090 A | 6/1960 | Diehl |
| 3,581,266 A | 5/1971 | Weyenberg |
| 4,037,082 A | 7/1977 | Tamada et al. |
| 4,067,692 A | 1/1978 | Farris |
| 4,549,250 A | 10/1985 | Spector |
| 4,629,604 A | 12/1986 | Spector |
| 4,714,984 A | 12/1987 | Spector |
| 4,785,642 A | 11/1988 | Chin et al. |
| 4,804,821 A | 2/1989 | Glucksman |
| 4,849,606 A | 7/1989 | Martens, III et al. |
| 4,853,517 A | 8/1989 | Bowen et al. |
| 5,014,913 A | 5/1991 | Hoyt et al. |
| 5,111,477 A | 5/1992 | Muderlak et al. |
| 5,136,684 A | 8/1992 | Lonker et al. |
| 5,175,791 A | 12/1992 | Muderlak et al. |
| 5,213,523 A | 5/1993 | Hygema et al. |
| 5,402,517 A | 3/1995 | Gillett et al. |
| 5,521,357 A | 5/1996 | Lock et al. |
| 5,556,192 A | 9/1996 | Wang |

(Continued)

FOREIGN PATENT DOCUMENTS

DE  199551632 A1  5/2000
EP  0691269 A1  1/1996

(Continued)

OTHER PUBLICATIONS

PCT/US2011/053616 International Search Report dated Mar. 7, 2012.

(Continued)

*Primary Examiner* — Michael Laflame, Jr.

(57) ABSTRACT

A volatile material dispensing system includes a frame having a front face and a rear face. A first magnetic element is disposed on the frame. A reservoir containing a volatile material is provided. A second magnetic element is disposed on the reservoir.

7 Claims, 15 Drawing Sheets

(56) References Cited

U.S. PATENT DOCUMENTS

| | | | |
|---|---|---|---|
| 5,574,821 A | 11/1996 | Babasade | |
| 5,577,156 A | 11/1996 | Costello | |
| 5,647,052 A | 7/1997 | Patel et al. | |
| 5,735,460 A | 4/1998 | Eisenbraun | |
| 5,788,155 A | 8/1998 | Martin et al. | |
| 5,845,847 A | 12/1998 | Martin et al. | |
| 5,882,256 A | 3/1999 | Shropshire | |
| 5,937,140 A | 8/1999 | Leonard et al. | |
| 5,945,094 A | 8/1999 | Martin et al. | |
| 5,976,503 A | 11/1999 | Martin et al. | |
| 6,072,165 A | 6/2000 | Feldman | |
| 6,085,026 A | 7/2000 | Hammons et al. | |
| 6,097,881 A | 8/2000 | DeWitt et al. | |
| 6,104,866 A | 8/2000 | DeWitt et al. | |
| 6,123,935 A | 9/2000 | Wefler et al. | |
| 6,141,496 A | 10/2000 | Sundberg et al. | |
| 6,289,176 B1 | 9/2001 | Martter et al. | |
| 6,293,474 B1 | 9/2001 | Helf et al. | |
| 6,296,196 B1 | 10/2001 | Denen et al. | |
| 6,302,559 B1 | 10/2001 | Warren | |
| 6,341,732 B1 | 1/2002 | Martin et al. | |
| 6,361,752 B1 * | 3/2002 | Demarest et al. | 422/306 |
| 6,378,780 B1 | 4/2002 | Martens, III et al. | |
| 6,382,522 B2 | 5/2002 | Tomkins et al. | |
| 6,386,462 B1 | 5/2002 | Martens, III | |
| 6,431,400 B1 | 8/2002 | O'Maley et al. | |
| 6,439,474 B2 | 8/2002 | Denen | |
| 6,446,880 B1 | 9/2002 | Schram et al. | |
| 6,450,419 B1 | 9/2002 | Martens, III et al. | |
| D463,736 S | 10/2002 | Hern | |
| D463,737 S | 10/2002 | Hern | |
| D464,416 S | 10/2002 | von Dohlen et al. | |
| 6,478,440 B1 | 11/2002 | Jaworski et al. | |
| 6,482,863 B2 | 11/2002 | Munagavalasa et al. | |
| D471,087 S | 3/2003 | McCoy et al. | |
| 6,569,387 B1 | 5/2003 | Furner et al. | |
| RE38,150 E | 6/2003 | Greatbatch et al. | |
| 6,609,935 B2 | 8/2003 | Huang | |
| 6,627,857 B1 | 9/2003 | Tanner et al. | |
| 6,630,110 B2 | 10/2003 | Urfig | |
| 6,631,852 B1 | 10/2003 | O'Leary | |
| 6,706,988 B1 | 3/2004 | Helf et al. | |
| 6,714,725 B2 | 3/2004 | Grone et al. | |
| 6,752,327 B2 | 6/2004 | Martens, III et al. | |
| 6,768,865 B2 | 7/2004 | Stathakis et al. | |
| 6,786,427 B2 | 9/2004 | Schram et al. | |
| 6,789,741 B2 | 9/2004 | Varanasi et al. | |
| 6,790,408 B2 | 9/2004 | Whitby et al. | |
| 6,793,149 B2 | 9/2004 | Schramm et al. | |
| 6,810,204 B2 | 10/2004 | Grone et al. | |
| 6,843,430 B2 | 1/2005 | Boticki et al. | |
| 6,853,801 B2 | 2/2005 | Wefler | |
| 6,857,580 B2 | 2/2005 | Walter et al. | |
| 6,859,615 B2 | 2/2005 | Yip et al. | |
| 6,894,193 B2 | 5/2005 | Zehner et al. | |
| 6,917,754 B2 | 7/2005 | Pedrotti et al. | |
| 6,957,012 B2 | 10/2005 | He et al. | |
| 6,969,008 B2 | 11/2005 | Helf et al. | |
| 6,996,335 B2 | 2/2006 | Zobele | |
| 7,017,829 B2 | 3/2006 | Martens, III et al. | |
| 7,028,861 B2 | 4/2006 | Sayers et al. | |
| 7,046,919 B2 | 5/2006 | Shimizu et al. | |
| 7,070,121 B2 | 7/2006 | Schramm et al. | |
| 7,088,914 B2 | 8/2006 | Whittle et al. | |
| D532,093 S | 11/2006 | Helf et al. | |
| 7,152,809 B2 * | 12/2006 | Ketcha et al. | 239/13 |
| D534,640 S | 1/2007 | Helf et al. | |
| 7,252,244 B2 | 8/2007 | Martens, III | |
| 7,277,626 B2 | 10/2007 | Pesu et al. | |
| 7,344,123 B2 | 3/2008 | Pankhurst et al. | |
| 7,389,943 B2 | 6/2008 | Jaworski | |
| 7,621,401 B2 | 11/2009 | Alegre de Miquel | |
| 7,621,426 B2 | 11/2009 | Reynolds et al. | |
| 7,661,929 B1 | 2/2010 | McVay | |
| 2002/0023639 A1 | 2/2002 | Ivri et al. | |
| 2004/0033171 A1 | 2/2004 | Kvietok et al. | |
| 2004/0124988 A1 | 7/2004 | Leonard et al. | |
| 2006/0000920 A1 | 1/2006 | Leonard | |
| 2006/0131329 A1 | 6/2006 | Sayers et al. | |
| 2006/0196965 A1 * | 9/2006 | Christianson et al. | 239/60 |
| 2006/0237439 A1 | 10/2006 | Norwood et al. | |
| 2007/0058956 A1 * | 3/2007 | Bankers et al. | 392/386 |
| 2007/0072140 A1 | 3/2007 | Almodovar | |
| 2007/0075159 A1 | 4/2007 | Lin | |
| 2007/0248502 A1 | 10/2007 | Adair et al. | |
| 2008/0013932 A1 * | 1/2008 | He et al. | 392/390 |
| 2008/0023568 A1 | 1/2008 | Weggelaar et al. | |
| 2008/0070025 A1 * | 3/2008 | Pavlin | 428/304.4 |
| 2008/0169355 A1 | 7/2008 | Pohl et al. | |
| 2009/0108094 A1 * | 4/2009 | Ivri | 239/101 |
| 2009/0127282 A1 | 5/2009 | Reynolds et al. | |
| 2009/0148142 A1 * | 6/2009 | McGee et al. | 392/387 |
| 2009/0236440 A1 | 9/2009 | Anderson et al. | |

FOREIGN PATENT DOCUMENTS

| | | | |
|---|---|---|---|
| EP | 1283062 A1 | | 2/2003 |
| EP | 2 308 340 A1 | | 4/2011 |
| EP | 2308340 | * | 4/2011 |
| EP | 2308340 A1 | * | 4/2011 |
| EP | 2308340 A1 | | 4/2011 |
| FR | 1596401 | | 6/1970 |
| GB | 936027 | | 9/1963 |
| GB | 2228681 A | | 9/1990 |
| GB | 2275609 A | | 9/1994 |
| GB | 2401548 A | | 11/2004 |
| JP | 06320083 | | 11/1994 |
| JP | 10 057464 A | | 3/1998 |
| JP | 10057464 A | | 3/1998 |
| WO | 9633946 A1 | | 10/1996 |
| WO | 0220172 A1 | | 3/2002 |
| WO | 02078750 A1 | | 10/2002 |
| WO | 03070287 A1 | | 8/2003 |
| WO | 2007048178 A1 | | 5/2007 |
| WO | 2007110086 A1 | | 10/2007 |
| WO | PCT/US11/053616 | | 2/2012 |

OTHER PUBLICATIONS

International Search Report and Written Opinion dated Aug. 10, 2007, Application No. PCT/US2007/008119.

* cited by examiner

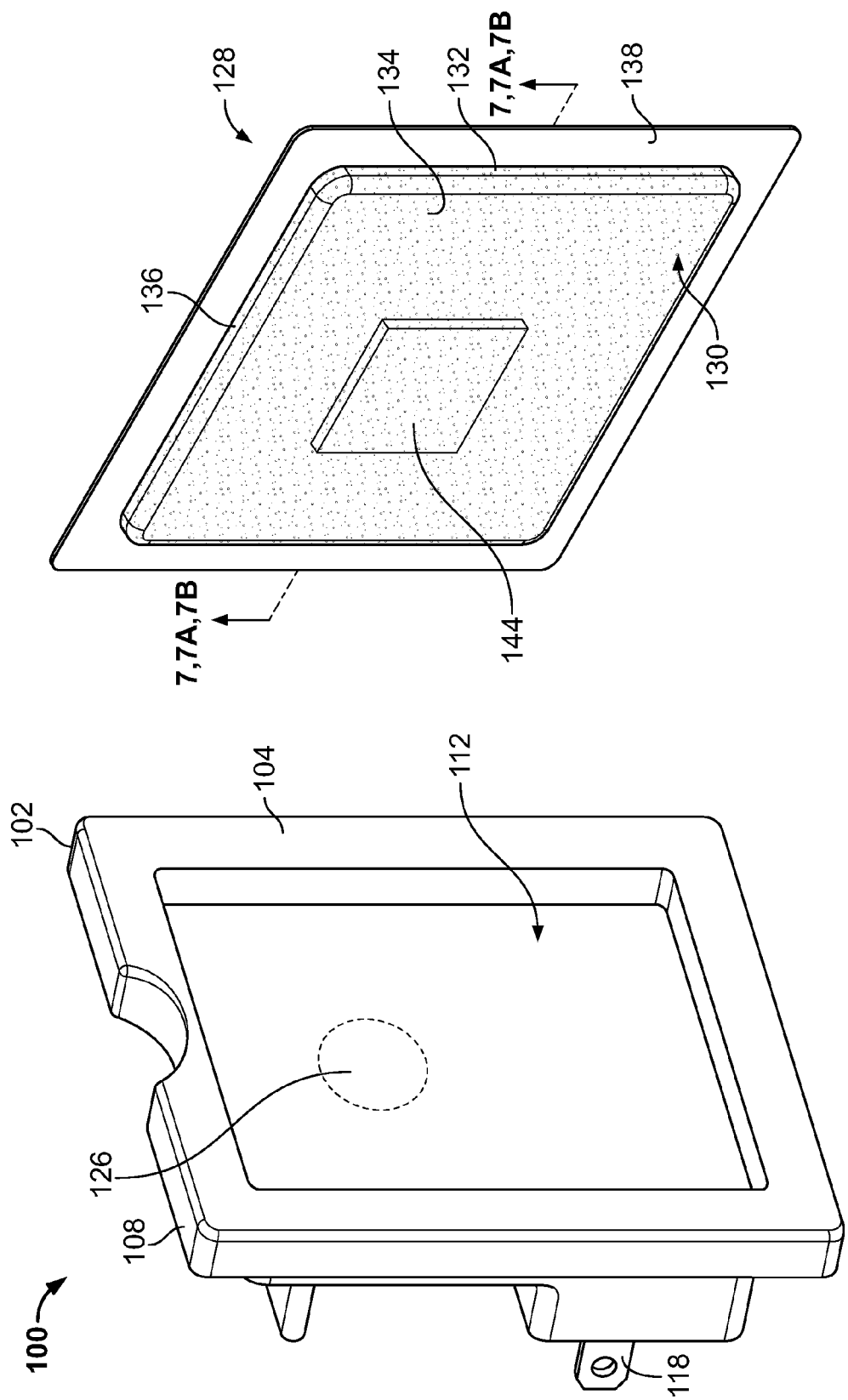

DISPENSING DEVICE

CROSS REFERENCE TO RELATED APPLICATIONS

Not Applicable

REFERENCE REGARDING FEDERALLY SPONSORED RESEARCH OR DEVELOPMENT

Not Applicable

SEQUENTIAL LISTING

Not Applicable

BACKGROUND OF THE INVENTION

1. Field of the Invention

The present invention generally relates to a device for a volatile material, and more particularly, to a device having a retention structure for securing a removable cartridge with a volatile material.

2. Description of Related Art

Dispensing devices are generally known. Some dispensing devices release volatiles into the atmosphere from pressurized systems using activation mechanisms. Other prior art dispensing devices use pump mechanisms to dispense volatiles into the atmosphere. Still other dispensing devices use heating mechanisms to assist in the volatilization of a product. Further, some dispensing devices rely on porous wicks and/or ambient air to dispense volatiles into the atmosphere via evaporation.

Many dispensing devices dispense product from refillable or replaceable product containers. Typically, product containers must be secured to the dispensing device in order to ensure proper operation. Common retention mechanisms traditionally include housing enclosures, fitted seats, slides, flanges, and the like. Additionally, a product container must be properly configured to work with the dispensing device to ensure effective operation. Some prior art systems use sensors to determine whether a product container is properly configured to work with the dispensing device. Other systems use electronic circuitry or electromagnetic locks.

The present disclosure contemplates various means of securing a refillable or replaceable product container to a dispensing device. The disclosed embodiments allow for the proper configuration and easy retention of a product container. Further, the embodiments provide for the effective diffusion of volatiles into the atmosphere. Several of the embodiments disclosed herein further utilize convenient frames and/or other structures to allow for easy conversion from active to passive emission or vice versa.

BRIEF SUMMARY OF THE INVENTION

According to one embodiment, a volatile material dispensing system includes a frame having a front face and a rear face. A first magnetic element is disposed on the frame. A reservoir containing a volatile material is provided. A second magnetic element is disposed on the reservoir.

According to another embodiment, a volatile material container includes a blister having a bottom wall, a peripheral flange, and a sidewall extending therebetween. A vapor permeable membrane is attached to the peripheral flange and extends across the blister. The vapor permeable membrane in conjunction with the bottom wall and the sidewall contains a volatile material within the blister. A magnetic element is disposed within the blister.

According to a different embodiment, a volatile material dispenser includes a frame having a front face, a rear face, and a sidewall therebetween. A recess is disposed within the rear face. A heating element is disposed within the recess of the rear face. An electrical outlet is in electrical communication with the heating element. A magnetic element is disposed on the frame.

BRIEF DESCRIPTION OF THE DRAWINGS

FIG. 1 is a front isometric view of a first embodiment of a dispensing device;

FIG. 2 is a rear isometric view of a volatile material container for use with the dispensing device of FIG. 1;

Other aspects and advantages of the present invention will become apparent upon consideration of the following detailed description, wherein similar structures have similar reference numerals.

DETAILED DESCRIPTION OF THE INVENTION

Figure 3:
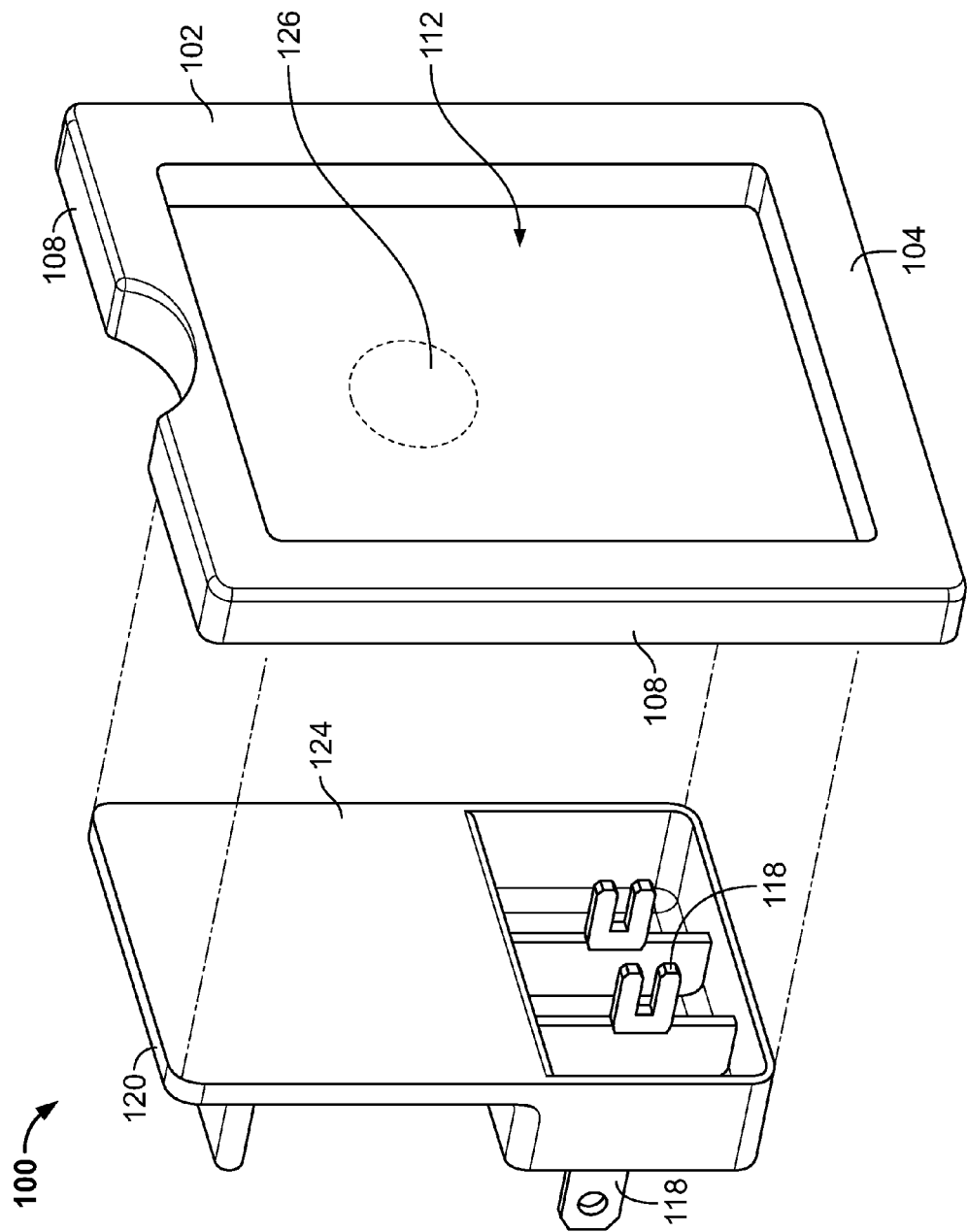
FIG. 3 is an exploded front isometric view of the dispensing device of FIG. 1.

As illustrated in FIGS. 1-7, a dispensing device 100 is presented. The dispensing device 100 includes a frame 102 having a front face 104, a rear face 106, and four sidewalls 108. The four sidewalls 108 are preferably equidistant in length and width and are substantially perpendicularly disposed in relation to the front and rear faces 104, 106. While the presently depicted frame 102 is generally square in cross-section, the frame 102 may be designed to comprise any number of shapes including, but not limited to, rectangular, oval, or pyramidal shapes. The frame 102 is preferably constructed from an injection-molded plastic, but may alternatively be constructed from a variety of compositions, including glass or copolyester resins.

Figure 4:
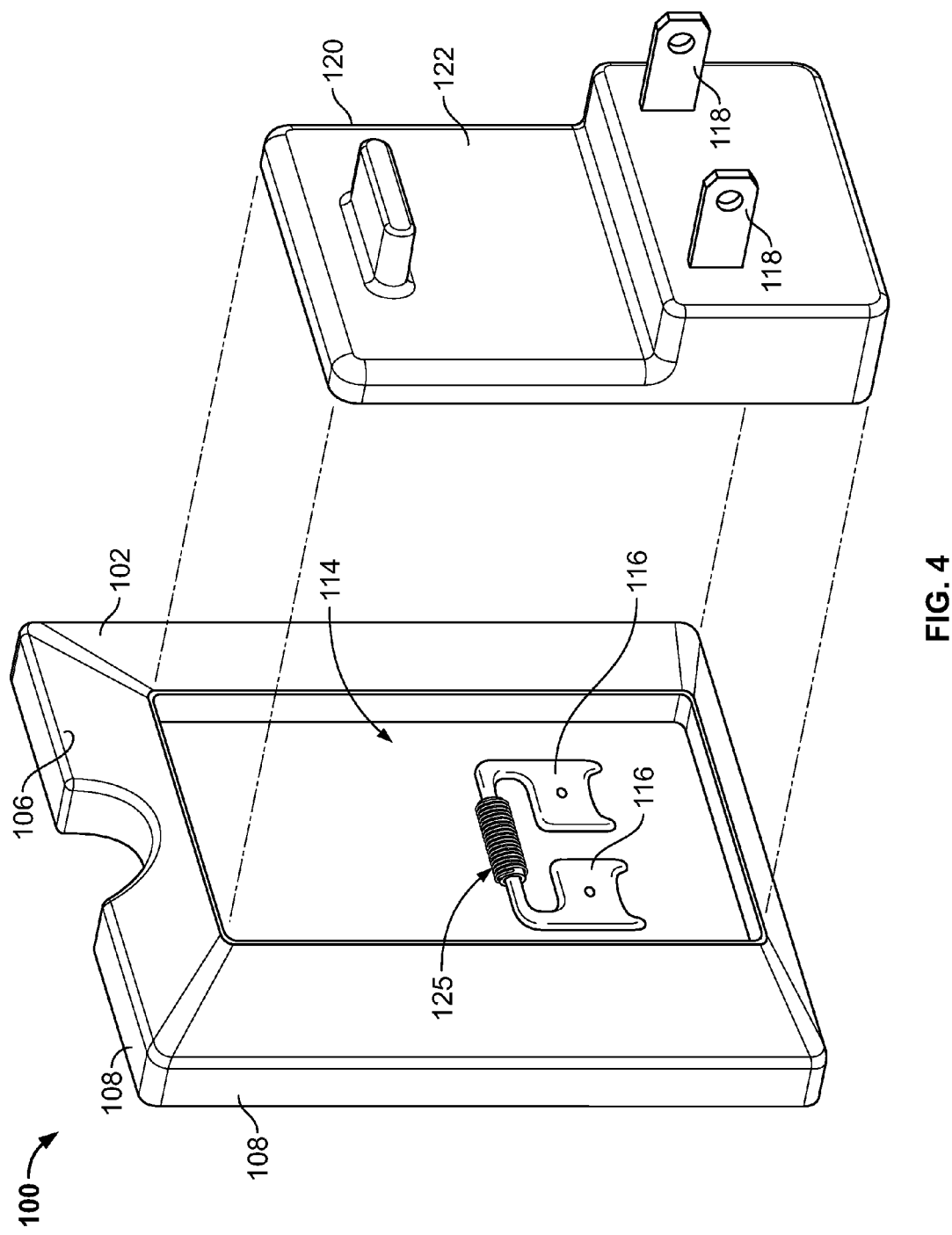
FIG. 4 is an exploded rear isometric view of the dispensing device of FIG. 1.
Figure 5:
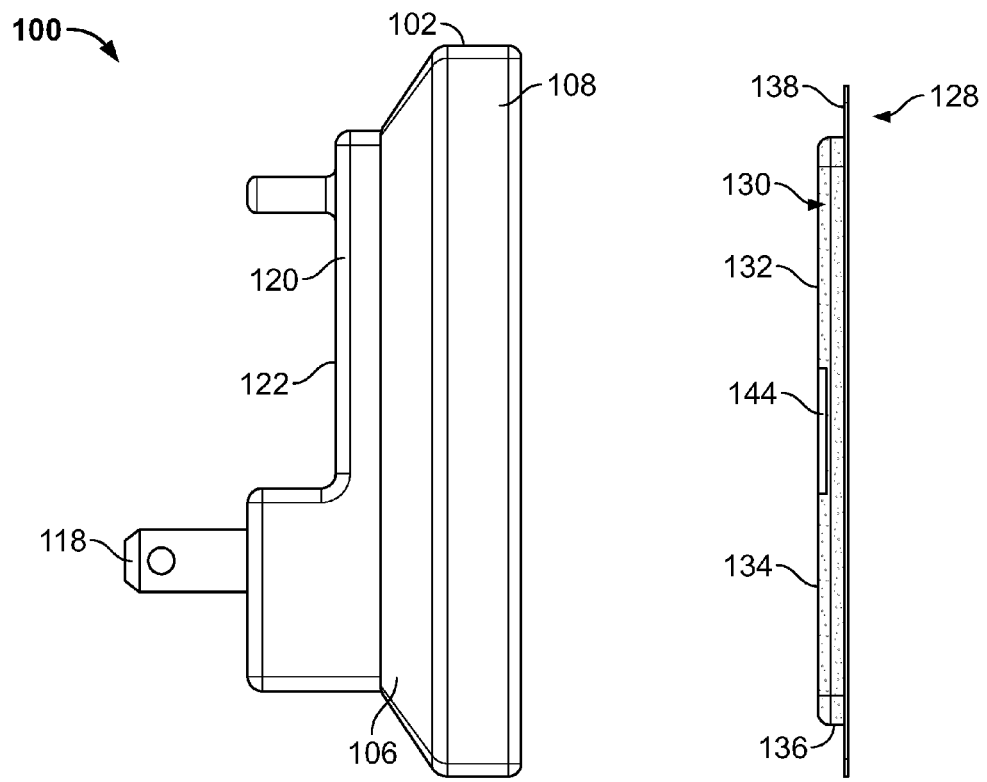
FIG. 5 is a side elevational view of the dispensing device of FIG. 1 and the volatile material container of FIG. 2.
Figure 6:
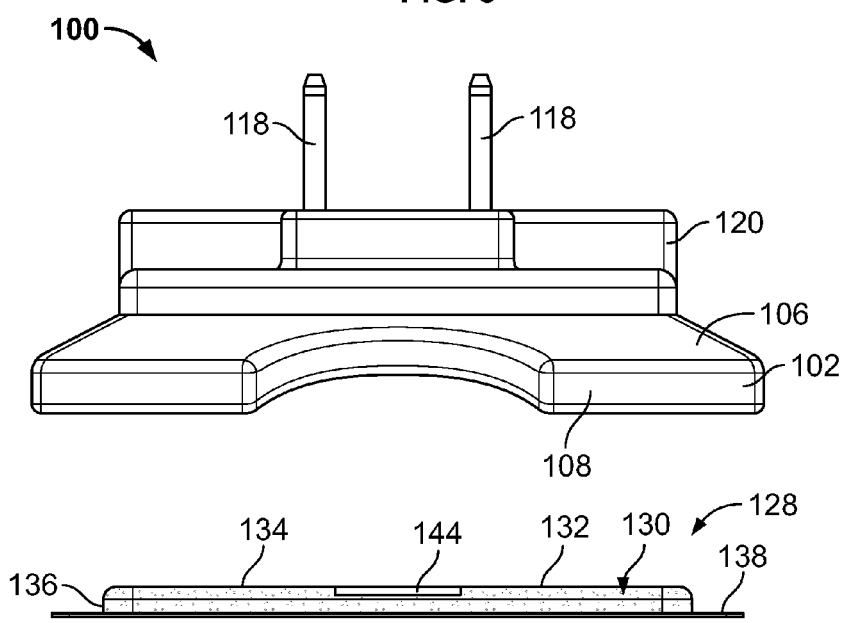
FIG. 6 is a top plan view of the dispensing device and volatile material container of FIG. 5.

The front face 104 and the rear face 106 include a front recess 112 and a rear recess 114, respectively. As seen in FIGS. 3 and 4, electrical leads 116 are disposed within the rear recess 114. The electrical leads 116 are configured to connect to electrical prongs 118 of an electrical plate 120. The electrical plate 120 is attached to the rear face 106 by an adhesive, one or more fasteners, a friction fit between portions of the electrical plate 120 and the portions of the frame 102 defining the rear recess 114, or by any other mechanism known to those of skill in the art. Alternatively, the electrical plate 120 may be integral with the rear face 106 of the frame 102. The electrical plate 120 is generally rectangular in shape and includes a front surface 122 and a rear surface 124. The electrical prongs 118 extend substantially perpendicularly from the rear surface 124 of the electrical plate 120 to the front surface 122 thereof. The electrical prongs 118 are adapted to be inserted into a traditional wall outlet (not shown) to provide power to the dispensing device 100. It will be apparent to one of skill in the art that the electrical prongs 118 may be modified to service varying types of outlets.

The electrical leads 116 provided within the rear recess 114 are in electrical communication with a heating element 125. The heating element 125 is preferably a ceramic covered resistor. However, it is envisioned that any other type of heating element may be used in conjunction with the present embodiments. The heating element 125 is substantially centrally disposed within the rear recess 114. In other embodiments, the heating element 125 is off-centered from the position shown in FIG. 4. Further, the heating element 125 may extend fully or partially a width and/or height of the rear recess 114 in other embodiments. Still further, a plurality of heating elements 125 may be provided in electrical communication with the electrical leads 116. It is also contemplated that one or more of the heating element 125 and the electrical leads 116 may be positioned within the frame 102 or fully or partially within or on the front or rear faces 104, 106 of the frame 102.

In another embodiment, the electrical plate 120 may include a battery housing (not shown) in lieu of the electrical prongs 118. In a further embodiment, the electrical plate 120 may include both a battery housing and the electrical prongs 118. In yet another alternative embodiment, the electrical plate 120 may include electrical prongs 118 and a rechargeable battery (not shown). In a further alternative embodiment, the electrical prongs 118 may be hingedly attached to the electrical plate 120 so that they may be folded into the dispensing device 100.

With reference to FIGS. 1 and 3, a first magnetic element 126 is disposed within an interior of the frame 102 between the front and rear recesses 112, 114. The first magnetic element 126 of the present embodiment is depicted as being provided above the heating element 125 and substantially centrally disposed about a width of the frame 102. However, in a different embodiment, the first magnetic element 126 may extend fully or partially a width and/or height of the frame 102. Further, in a different embodiment, the first magnetic element 126 is provided within the frame 102 in alignment with the heating element 125. In the present embodiment, the first magnetic element 126 is circular shape. However, the first magnetic element 126 may also comprise any other geometric shape including, but not limited to, rectangular, spherical, oval, elliptical, or pyramidal shapes.

Figure 8:
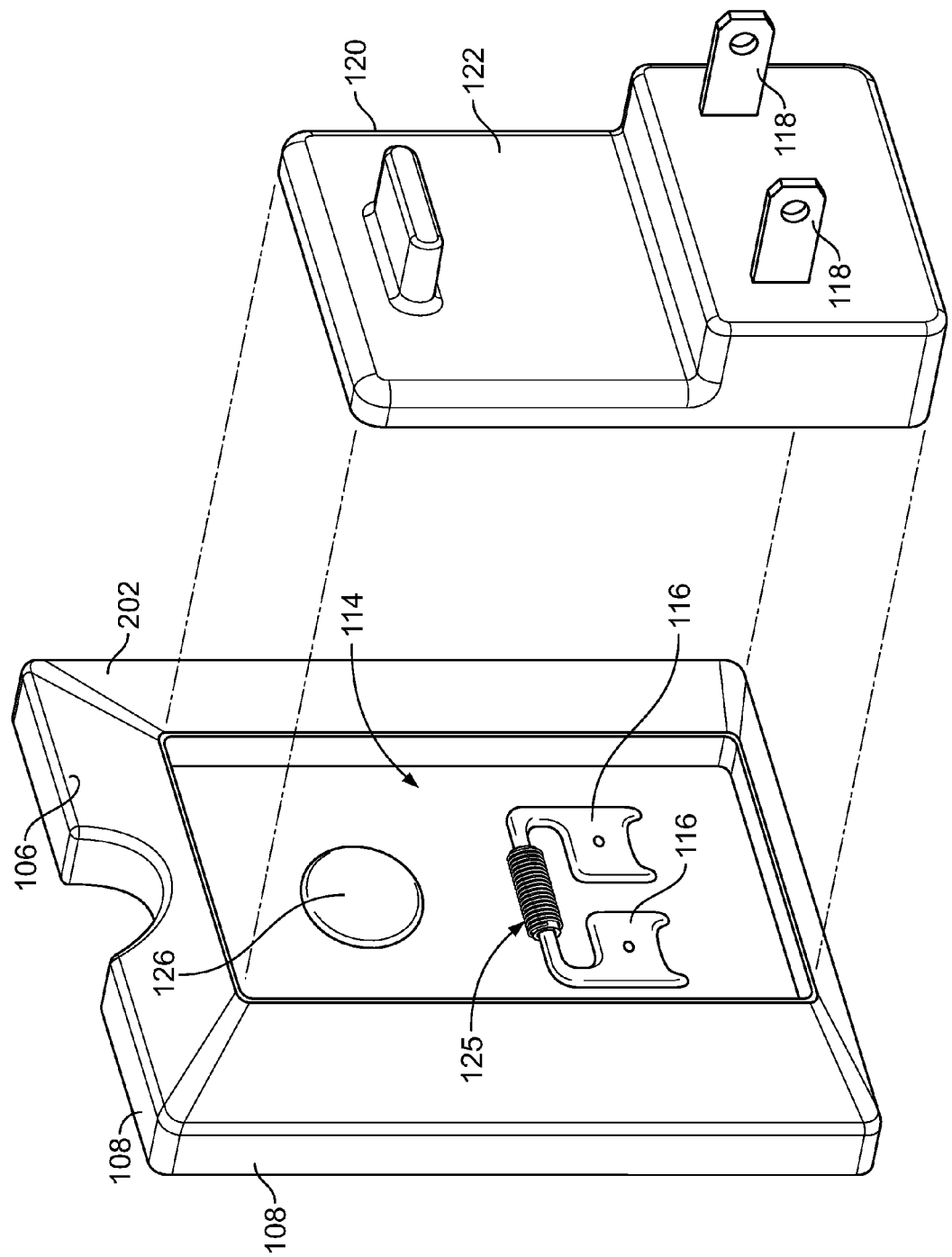
FIG. 8 is an exploded rear isometric view of a dispensing device similar to the one depicted in FIG. 4, wherein a first magnetic element is provided within a rear recess of a frame of the device.

The first magnetic element 126 of the present embodiment is shown within a wall comprising the frame 102 between the front and rear recesses 112, 114. The first magnetic element 126 may be formed within the frame 102 during the manufacturing process, provided within a bore or recess in one of the front or rear faces 104, 106 (not shown), placed between two separable portions of the frame 102 (not shown), or provided within the frame 102 in any manner known to one of skill in the art. It is also intended that the first magnetic element may be disposed on a surface of the frame 102 defining a portion of the front or rear recesses 112, 114. For example, the first magnetic element 126 depicted in FIGS. 1 and 3 may instead represent a magnetic element attached to a wall defining a portion of the front recess 112. The first magnetic element 126 of this embodiment may be placed directly on the wall or within a bore or recess and held in place by an adhesive, a friction fit between portions of the first magnetic element 128 and portions of the frame 102, or by any other mechanism of securement known to those of skill in the art. Similarly, FIG. 8 depicts an alternative embodiment of a frame 202, wherein the first magnetic element 126 is disposed within the rear recess 114 of the frame 202.

Turning to FIGS. 1 and 2, the front recess 112 is configured to receive a volatile material container 128. The front recess 112 is preferably shaped in a complementary fashion to that of the container 128 so that same may be nested within the front recess 112. Now turning to FIGS. 2 and 5-7, the container 128 is presented with greater particularity. The container 128 contains a volatile material 130 within a blister 132, which is preferably a thermoformed structure. The container 128 includes a bottom wall 134 and sidewalls 136 that extend therefrom and terminate at a surrounding flange 138. The four sidewalls 136 are preferably the same length and width. Additionally, while the container 128 is depicted as having a square shape, the container 128 may be designed to comprise any number of shapes including, but not limited to, rectangular, oval, or pyramidal shapes. A vapor permeable membrane 140 is adhered to the surrounding flange 138 and extends across the blister 132 (see FIG. 7). The permeable membrane 140, in conjunction with the bottom wall 134 and the sidewalls 136, act to contain the volatile material 130 within the sealed reservoir of the blister 132. An impermeable laminate 142 is releasably adhered to the container 128 over the permeable membrane 140. While the impermeable laminate 142 is in place, the volatile material 130 is prevented (or substantially prevented) from diffusing into the atmosphere.

The volatile material 130 may comprise an active ingredient for diffusion into the surrounding atmosphere, such as a fragrance, air freshener, odor eliminator, or insect repellant or insecticide. The volatile material may be a liquid, a gel, a solid, a gas, a mix of the aforementioned forms, or any other form known to those of skill in the art. It is contemplated that any type of volatile material suited for dispersal through a permeable membrane may be used with the present embodiments described herein.

Illustratively, the permeable membrane 140 has a thickness of about 0.05 mm to about 0.15 mm and has a density within a range of about 0.88 to 0.95 grams/cubic centimeter. The permeable membrane 140 may also be formed integrally with the impermeable laminate 142 and is heat fused to the flange 138 such that the permeable membrane 140 extends across the entire blister 132. The permeable membrane 140 is a 5 layer co-extrusion, which includes first and second layers of a blend of low density polyethylene (LDPE) and ultra low density polyethylene (ULDPE) bonded to opposing sides of a first LDPE layer. A second LDPE layer is also bonded to the second LDPE/ULDPE layer and a polypropylene (PP) layer is bonded to the opposite side of the second LDPE layer. The permeable membrane 140 is preferably clear and translucent, allowing for visibility of the volatile material 130 therethrough.

The size of the permeable membrane 140 is a key factor in the diffusion rate of the volatile material 130 therethrough. The smaller the surface area of the permeable membrane 140, the less volatile material 130 that is released, which may result in lower fragrance intensity being detected by the consumer. Other factors that may influence the diffusion rate of the volatile material include the specific composition of the volatile material, the thickness and composition of the permeable membrane, and the amount of volatile material contained within the container 128.

The impermeable laminate 142 may include a layer of polypropylene, aluminum foil, and/or polyester. In one embodiment, the impermeable laminate includes a layer of aluminum foil, a layer of polypropylene (PP) adhered to one face of the aluminum foil by a PP adhesive, and a layer of polyethylene terephthalate (PET) bonded to another face of the aluminum foil. The PP layer of the foil cover is in contact with the PP layer of the vapor-permeable membrane when the foil cover is sealed thereto. Illustratively, the impermeable laminate 142 has a thickness of between about 0.1 mm and about 0.2 mm. The polyester layer is generally suitable for printing and may be the outer surface of the impermeable laminate 142.

Figure 7:
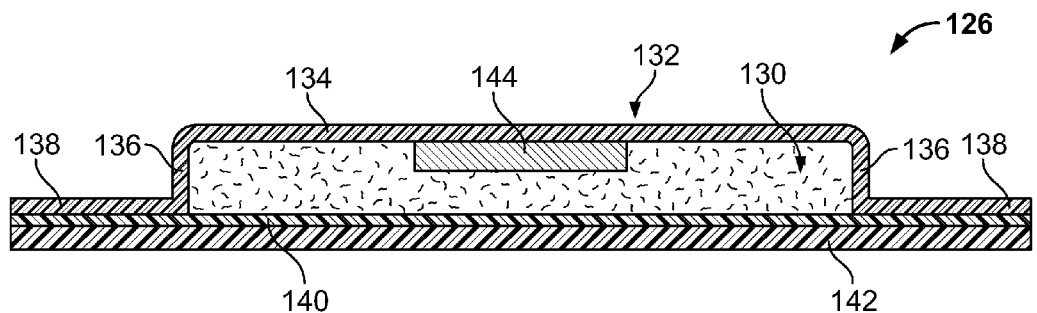
FIGS. 7, 7A, and 7B are partial sectional views of the volatile material container of FIG. 2 taken generally along the lines 7-7, 7A-7A, and 7B-7B, respectively, depicting various positions of second magnetic elements.
Figure 7A:
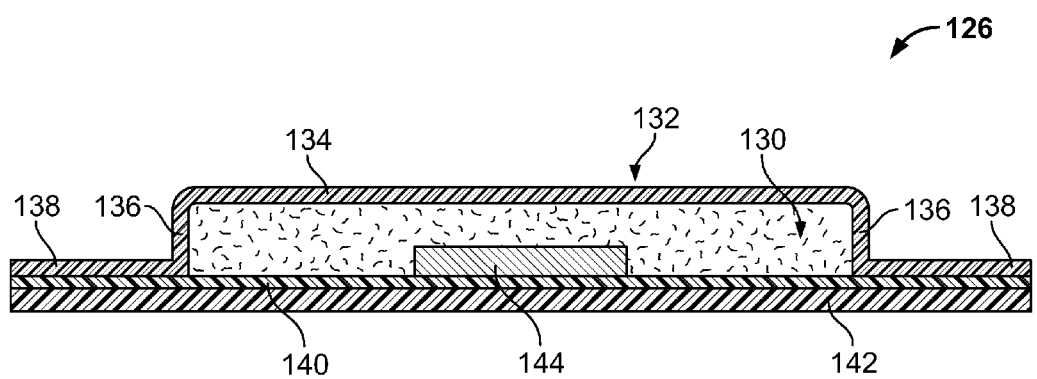
Figure 7B:
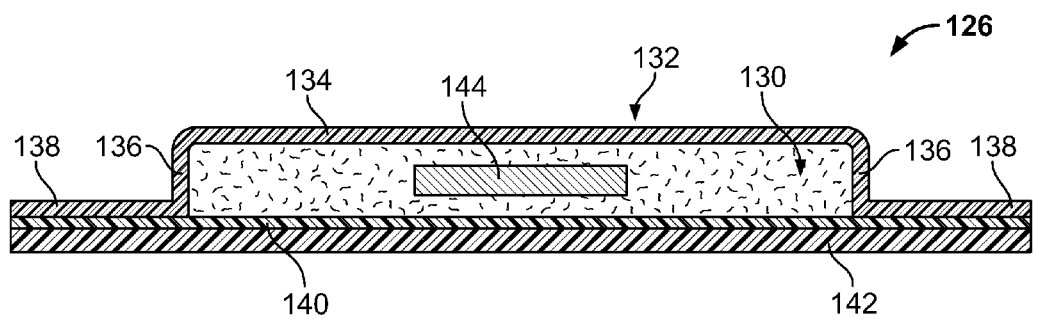

Turning again to FIGS. 2 and 5-7, it may be seen that the container 128 includes a second magnetic element 144. In the present embodiment, the second magnetic element 144 is attached to the bottom wall 134 of the blister 132. However, the second magnetic element could instead be attached to one or more of the sidewalls 136, the permeable membrane 140, or be provided unattached within the container 128 between the blister 132 and the permeable membrane 140 (see FIGS. 7A and 7B). In the present embodiment, the second magnetic element 144 is formed in the shape of a square. In other embodiments, the second magnetic element 144 may be designed to comprise any number of shapes including, but not limited to, rectangular, oval, or pyramidal shapes. When the container 128 is placed within or adjacent the front recess 112 of the frame 102, the second magnetic element 144 within the container 134 is magnetically attracted to the first magnetic element 126 in the frame 102. In this way, the container 128 is magnetically retained by the frame 102.

The magnetic elements described herein generally refer to materials or objects that produce and/or are attracted to a magnetic field. In a preferred embodiment, the first and second magnetic elements are both permanently magnetized, such that both the first and second magnetic elements maintain their own magnetic fields indefinitely or for substantially long periods of time. In another preferred embodiment, at least one of the first and second magnetic elements is a permanent magnet and the other of the first and second magnetic elements comprises a ferromagnetic material, such that the material may be magnetized by a magnetic field and/or attracted to materials that are magnetized. In yet another preferred embodiment, at least one of the first and second magnetic elements is an electromagnetic material, which produces a magnetic field or takes on the properties of a ferromagnetic material when an electric current passes through it. With respect to embodiments utilizing electromagnetic elements, it is contemplated that the electrical leads 116 may be in electrical communication with the first magnetic element 126. Further, the magnetic elements may consist of combinations of permanently magnetized materials, ferromagnetic materials, and/or electromagnetic materials.

If a container is placed within or adjacent the front recess 112 of the frame 102 that does not include a second magnetic element 144, the container will not be retained by the dispensing device 100. In this manner the dispensing device 100 prevents inadvertent use of containers, which may be incompatible with the device, e.g., the container may not be suited for withstanding heat from the heating element 125 or the container may include a volatile material incompatible with the environment the device is in, such as a pesticide in a bathroom. Indeed, it is also contemplated that varying refills with second magnetic elements 144 will only work with dispensing devices having compatible first magnetic elements. For example, one embodiment utilizes a frame 102 having an electromagnetic first element 140 that produces a magnetic field with a strength insufficient to retain a container with a second ferromagnetic element, but that is sufficient to retain a different container with a second permanent magnetic element. However, both of the previously noted ferromagnetic and permanent second magnetic elements may also be adapted to be retained by a frame 102 having a first permanent magnetic element. It is contemplated that one of skill in the art reading the present disclosure will understand how different magnetic elements with varying magnetic field strengths may be used to preclude inadvertent container usage with the various dispensing devices disclosed herein.

During a non-use state of the dispensing device 100, diffusion of the volatile material 130 from the container 128 through the impermeable laminate 142 is prevented (or substantially prevented) by the impermeable laminate 142. During an in use state, the impermeable laminate 142 is removed from the blister 132. A user removes the impermeable laminate 142 by grasping an end thereof and peeling it off the blister 132. A tab, extension, or other means for grasping (not shown) may be included as an extension of the impermeable laminate 142 to aid in removal of same. The extension (not shown) is preferably provided at a corner of the impermeable laminate 142, but may extend from any portion thereof. Following removal of the impermeable laminate 142 the container 128 transitions from a full or first condition toward an empty or second condition, which allows for the volatile material 130 to be dispersed into the atmosphere.

The dispensing device 100 of the present embodiment may dispense volatile material into the atmosphere actively or passively. In the passive state, a user removes the impermeable laminate 142 from the blister 132, but does not activate the heating device. This allows the dispensing device to passively emit the volatile material 130 from the blister 132 through the permeable membrane 140 and into the atmosphere unassisted. The dispensing device 100 may be electrically connected to an outlet with an activation switch, sensor, or other activation means (not shown) turned to an off position to allow for passive diffusion of the volatile material 130. Alternatively, the dispensing device 100 could be rested upon a support surface (not shown), such as a desk or table, to allow the passive diffusion of the volatile material 130.

In an active state, a user removes the impermeable laminate 142 from the blister 132 and activates the heating element 125 by plugging the electrical prongs 118 into a conventional wall outlet. In alternative embodiments, the dispensing device 100 may also include an activation switch, sensor, or other activation means (not shown) turned to an on position to activate the heating element 125 when plugged into a wall outlet. When in an active state, electrical energy is transferred from the wall outlet through the electrical prongs 118 and to the heating element 125. The heating element 125 converts the electrical energy into thermal energy. Thermal energy is conducted through a wall of the frame 102 between the heating element 125 and the container 128, and is thereafter conducted through the blister 132 and into the volatile material 130. The conduction of thermal energy throughout the dispensing device 100 acts to increase the volatilization of the volatile material 130 through the permeable membrane 140 and the active diffusion of the volatile material 130 into the atmosphere. The increased diffusion rate allows for a stronger concentration of the volatile material 130 in a given area and/or the ability to effectively disperse the volatile material 130 to a larger area. It has also been found that conduction of thermal energy through the first and/or second magnetic elements 126, 144 produces the surprising result of a further increased rate of volatilization of the volatile material 130. The first and second magnetic elements 126, 144 act as heat sinks to assist in spreading the thermal energy delivered by the heating element 125 to the container 128.

Figure 9:
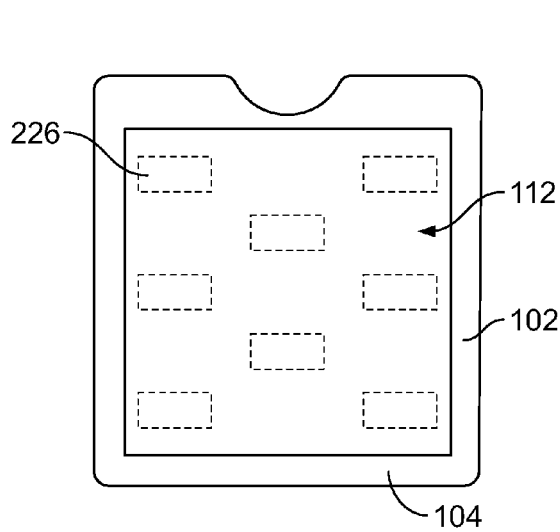
FIGS. 9-12 are front elevational views of the dispensing device of FIG. 1 depicting several different embodiments of first magnetic elements disposed within a frame of the device.
Figure 10:
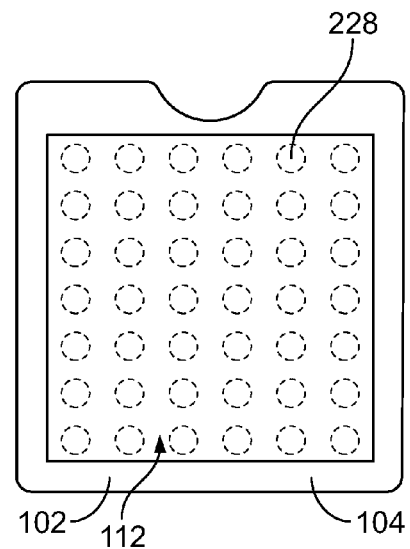
Figure 11:
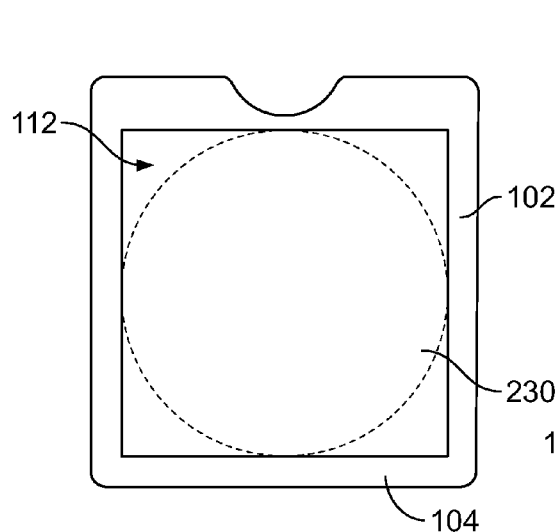
Figure 12:
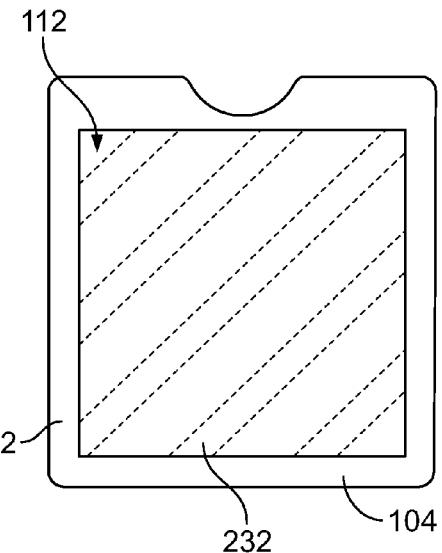

Various other embodiments or modifications to the previously described dispensing device 100 are also contemplated, which may include any of the structures or alternative structures as noted hereinabove. FIGS. 9-12 illustrate several views of the front face 104 of alternative embodiments of the frame 102 of the dispensing device 100, wherein the depicted first magnetic element(s) may be disposed within the frame or on the front or rear 104, 106 faces thereof. FIG. 9 depicts the frame 102 having multiple first magnetic elements 226 instead of a single first magnetic element 126. In the illustrated embodiment, the first magnetic elements 226 are depicted as flat rectangular strips of magnetic material. However, the first magnetic elements 226 may include any geometric shape, size, or positional pattern as previously noted herein and as may be provided for in the following embodiments. FIG. 10 illustrates another embodiment of the frame 102, wherein first magnetic elements 228 are embodied in small circular portions of magnetic material positioned in a matrix formation. FIG. 11 illustrates a further alternative embodiment of the frame 102 that includes a single first magnetic element 230 that spans the majority of the front recess 112. FIG. 12 depicts another alternative embodiment of the frame 102, which includes a plurality of first magnetic elements 232 in the shape of angled rectangular strips.

Figure 13:
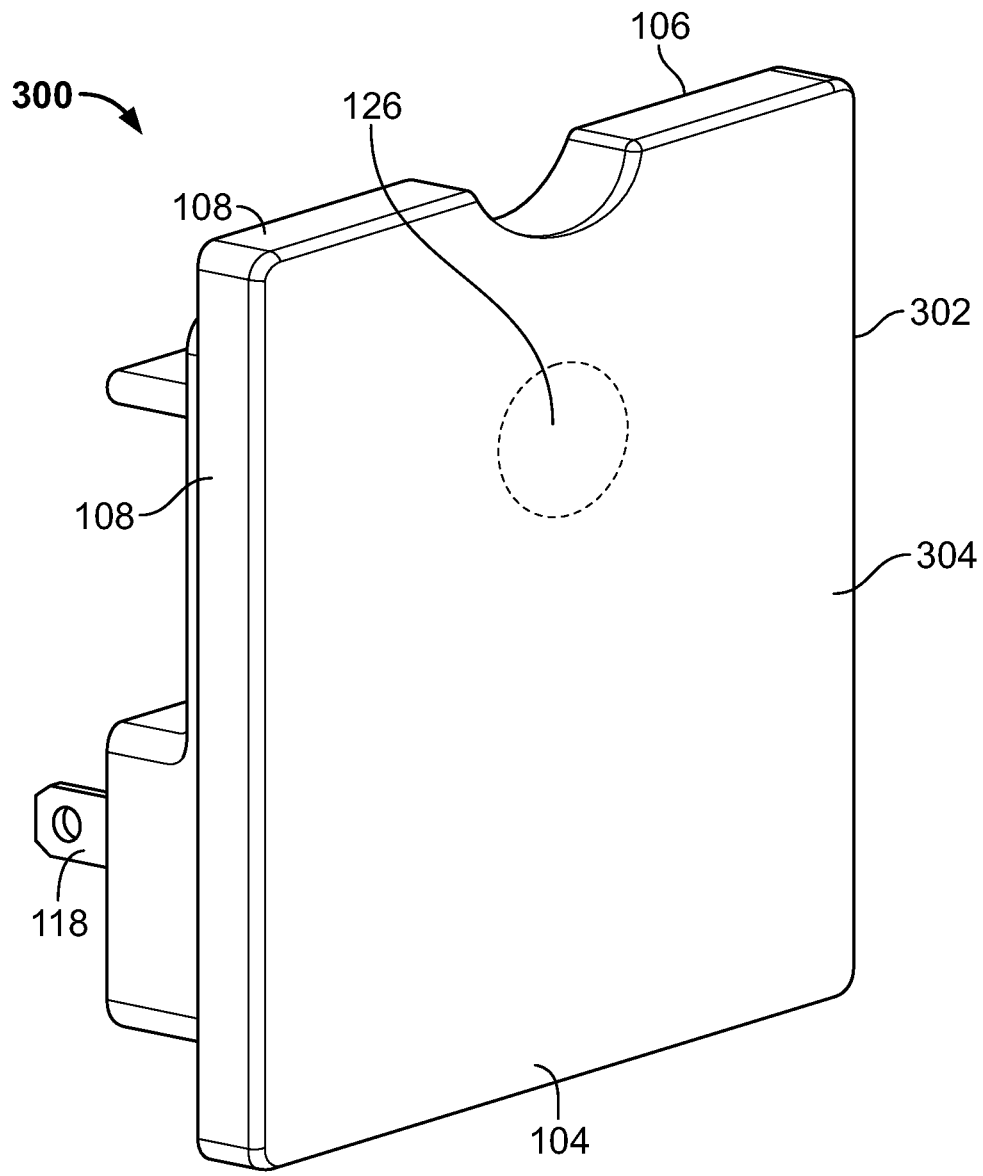
FIG. 13 is a front isometric view of an alternative embodiment of a dispensing device with a frame having a substantially planar front wall.

FIG. 13 illustrates a different embodiment of a dispensing device 300 similar to the dispensing device 100 except for the following differences. In lieu of the frame 102 with the front recess 112, a frame 302 is provided that does not include a recess. Rather, the front face 104 of the frame 302 comprises a substantially planar front wall 304. Similar to the previous embodiments noted herein, the first magnetic element 126 is positioned within the frame 302 or on the front or rear 104, 106 faces thereof. Further, while the first magnetic element 126 is depicted as a circular element centered about a width of the frame 302, the first magnetic element 126 of the present embodiment may comprise any geometric shape, size, or positional pattern as previously noted herein and as may be provided for in the following embodiments.

Figure 14:
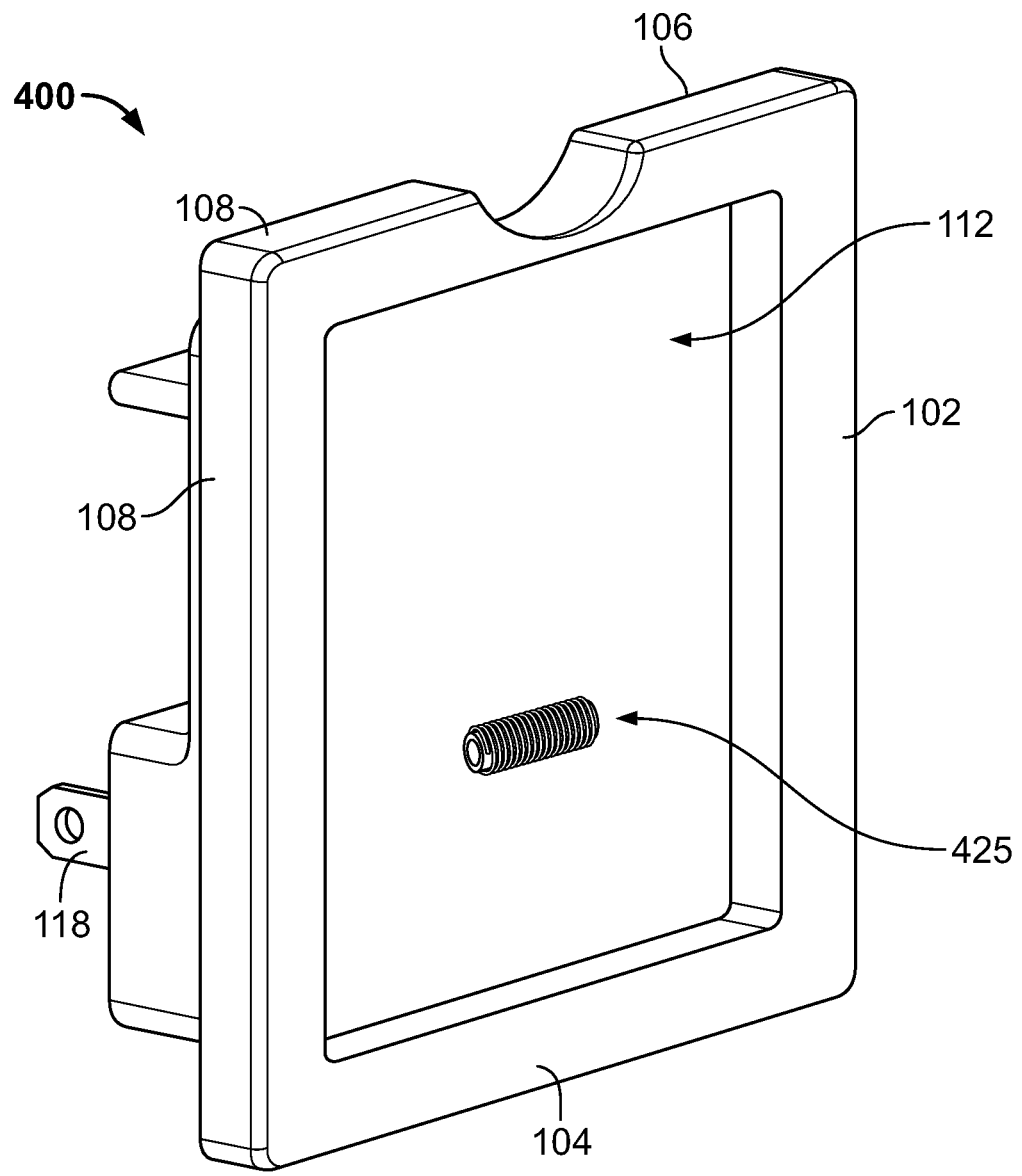
FIG. 14 is a front isometric view of another embodiment of a dispensing device, which does not include a first magnetic element on a frame thereof.

FIG. 14 illustrates yet another embodiment of a dispensing device 400 similar to the dispensing device 100 except for the below noted differences. In the present embodiment, the first magnetic element 126 is not provided. Instead, a heating element 425 provides heat in a similar manner as the heating element 125 with the additional functional advantage of operating as an electromagnet. When supplied with current, the heating element 425 produces a magnetic field to assist in coupling the dispensing device 400 with the second magnetic element 144 of the container 128. The heating element 425 is depicted as extending through the front face 104 of the frame 102 within the front recess 112. However, the heating element 425 may be attached to the frame 102 in any manner as noted herein, e.g., one or more of the heating element 425 and the electrical leads 116 may be positioned within the frame 102 or fully or partially within or on the front or rear faces 104, 106 of the frame 102. In other embodiments there may be several heating elements 425 that operate as one of several first magnetic elements. Additionally, the heating element 425 may produce a magnetic field even in the absence of electric current, or may be combined with other first magnetic elements that do not rely on electric current for their magnetic properties. Further, in other embodiments the dispensing device 300 depicted in FIG. 13 may be similarly modified.

Figures 15, 16:
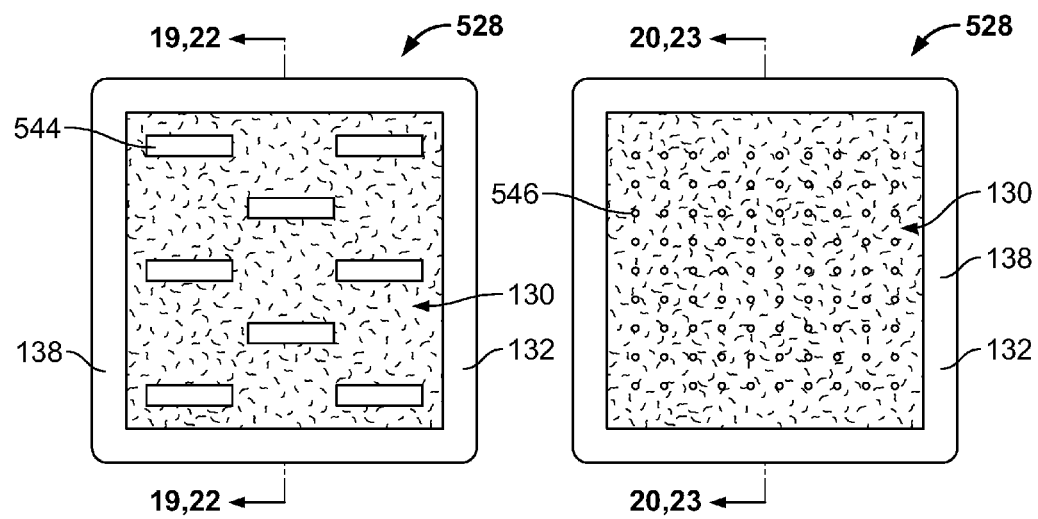
FIGS. 15-18 are front elevational views of different embodiments of volatile material containers similar to the one depicted in FIG. 2, depicting various positions of second magnetic elements.
Figures 17, 18:
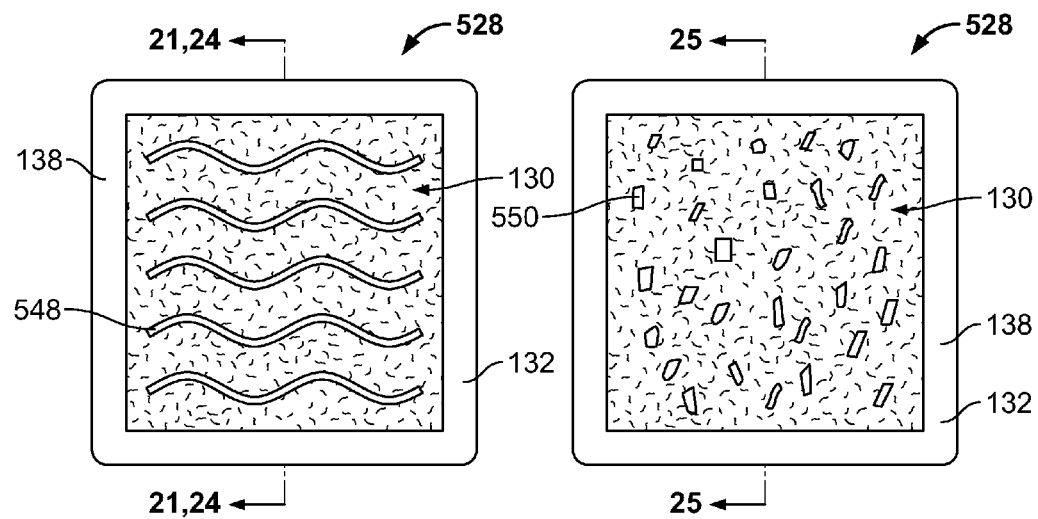
Figure 19:
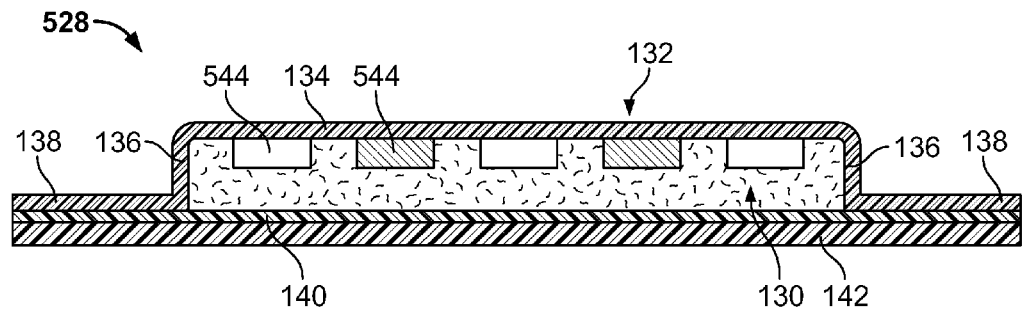
FIGS. 19-21 are partial sectional views of the volatile material container of FIGS. 15-17, respectively, wherein second magnetic elements are depicted attached to a bottom wall of the container.

FIGS. 15-18 illustrate alternative embodiments of the volatile material container 128, wherein the containers are similar except for the following differences. Referring to FIG. 19, a container 528 includes a plurality of second magnetic elements 544 as opposed to the single second magnetic element 144. In the present embodiment, the second magnetic elements 544 are formed into rectangular magnetic strips. FIG. 16 depicts a plurality of magnetic beads 546. FIG. 17 illustrates several magnetic threads 548. FIG. 18 provides for a plurality of magnetic flakes 550. It is anticipated that other forms of magnetic material may be similarly disposed within the container 528 as known to those of skill in the art.

Figure 20:
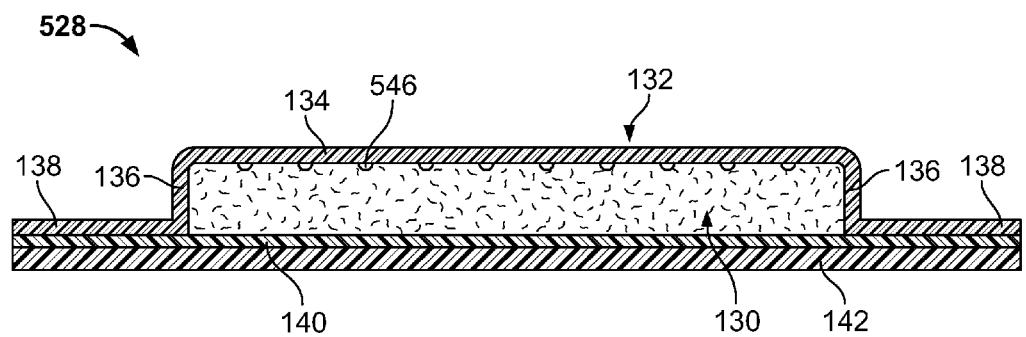
Figure 21:
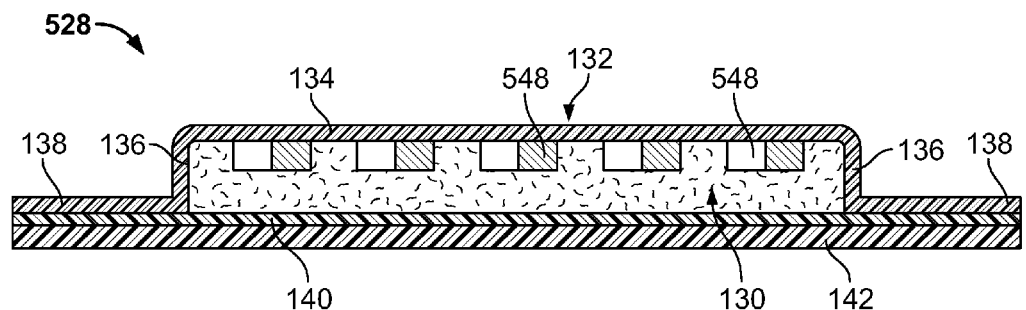
Figure 22:
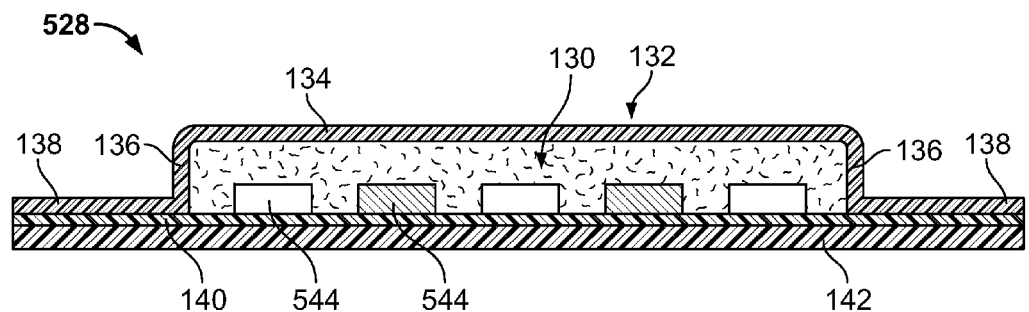
FIGS. 22-24 are partial sectional views of the volatile material container of FIGS. 15-17, respectively, wherein second magnetic elements are depicted attached to a permeable membrane of the container.
Figure 23:
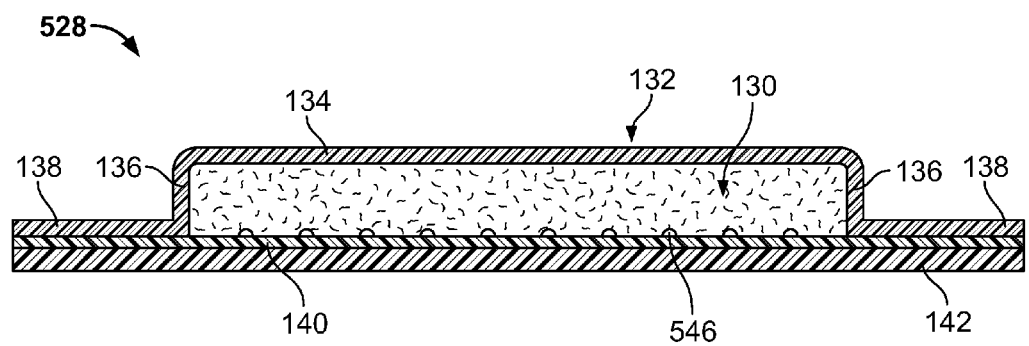
Figure 24:
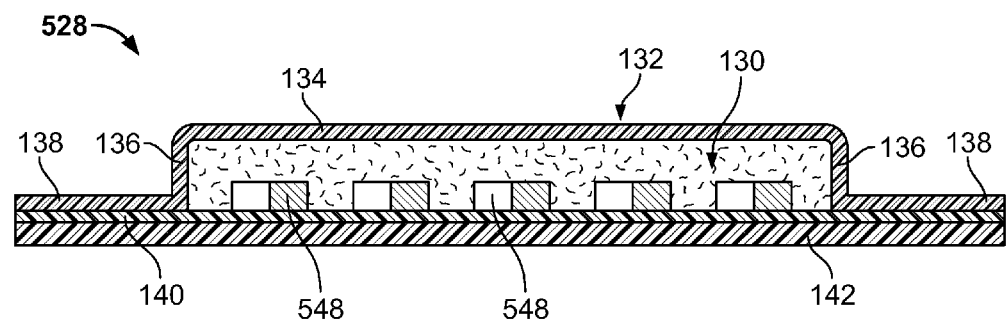
Figure 25:
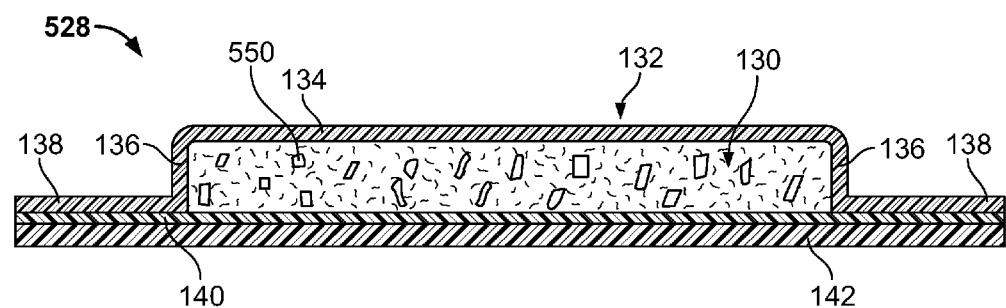
FIG. 25 is a partial sectional view of the volatile material container of FIG. 18, wherein second magnetic elements are depicted suspended within the container.

Turning to FIGS. 15-17, the second magnetic elements 544, 546, 548 are depicted in FIGS. 19-21, respectively, as being attached to the bottom wall 134 of the blister 132. Alternatively, FIGS. 22-24 depict the second magnetic elements 544, 546, 548 of FIGS. 15-17, respectively, attached to the permeable membrane 140 of the container 128. It is also contemplated that any of the second magnetic elements 544-550 could instead be attached to one or more of the sidewalls 136, the bottom wall 134, or the permeable membrane 140, be provided unattached within the container 128 between the blister 132 and the permeable membrane 140, or any combination thereof. For example, the second magnetic elements 550 depicted in FIG. 25 are preferably suspended within the volatile material 130 of the blister 132. In other embodiments, the second magnetic elements 544-550 may be designed to comprise any number of shapes or sizes. Advantageously, the second magnetic elements 544-550 serve to retain the volatile material container 528 within any of the above described frames. Further, in some embodiments the second magnetic elements 544-550 assist in the conduction of thermal energy from the heating element 125 to assist in the volatilization of the material 130 in the blister 132.

Figure 26:
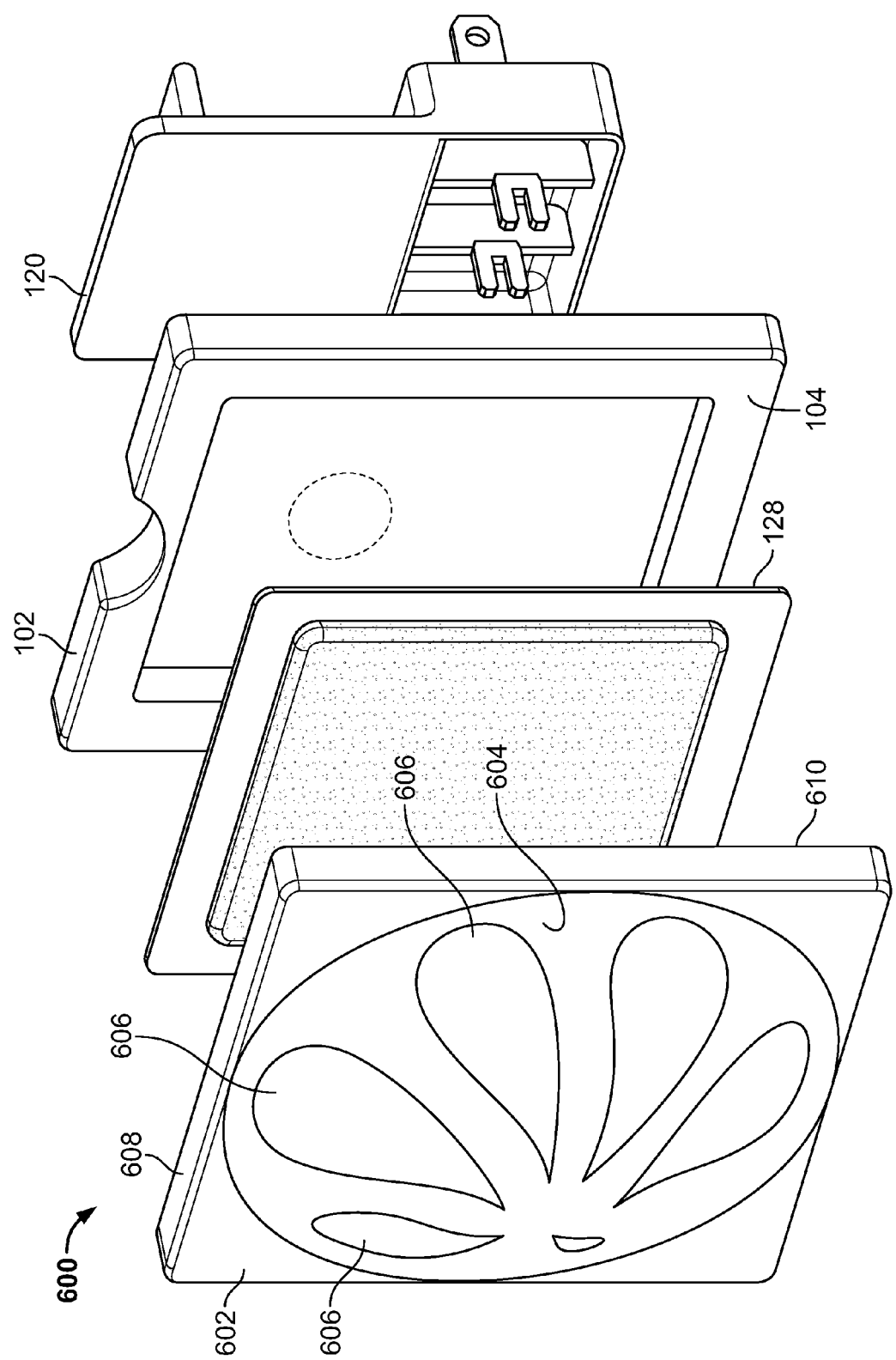
FIG. 26 is yet another embodiment of a dispensing device, which includes a cover plate with a bulbous protrusion.

FIG. 26 depicts an alternative embodiment of a dispensing device 600, which includes a generally square-shaped cover plate 602. The cover plate 602 includes a bulbous protrusion 604 having orifices 606 extending therethrough. A raised peripheral flange 608 extends around a rear side 610 of the cover plate 602. The frame 102 is releasably attached to the cover plate 602 by an interference fit between peripheral portions of the frame 102 and the raised peripheral flange 608 of the cover plate 602. In alternative embodiments, the cover plate 602 and the frame 102 are attached by a snap fit connection, an adhesive, screws, or in any other manner known to one of skill in the art.

Attachment of the cover plate 602 to the frame 102 defines a compartment therebetween. Specifically, the compartment comprises the space between the front face 104 of the frame 102 and the rear side 610 of the cover plate 602. During use, the volatile material container 128 is positioned in the compartment. The cover plate 602 is attached to the frame 102 such that the compartment defined therebetween accommodates the volatile material container 128. In other embodiments, the compartment or other portions of the cover plate 602 or the frame 102 may accommodate a fan (not shown) or other similar air circulation apparatus.

Figure 27:
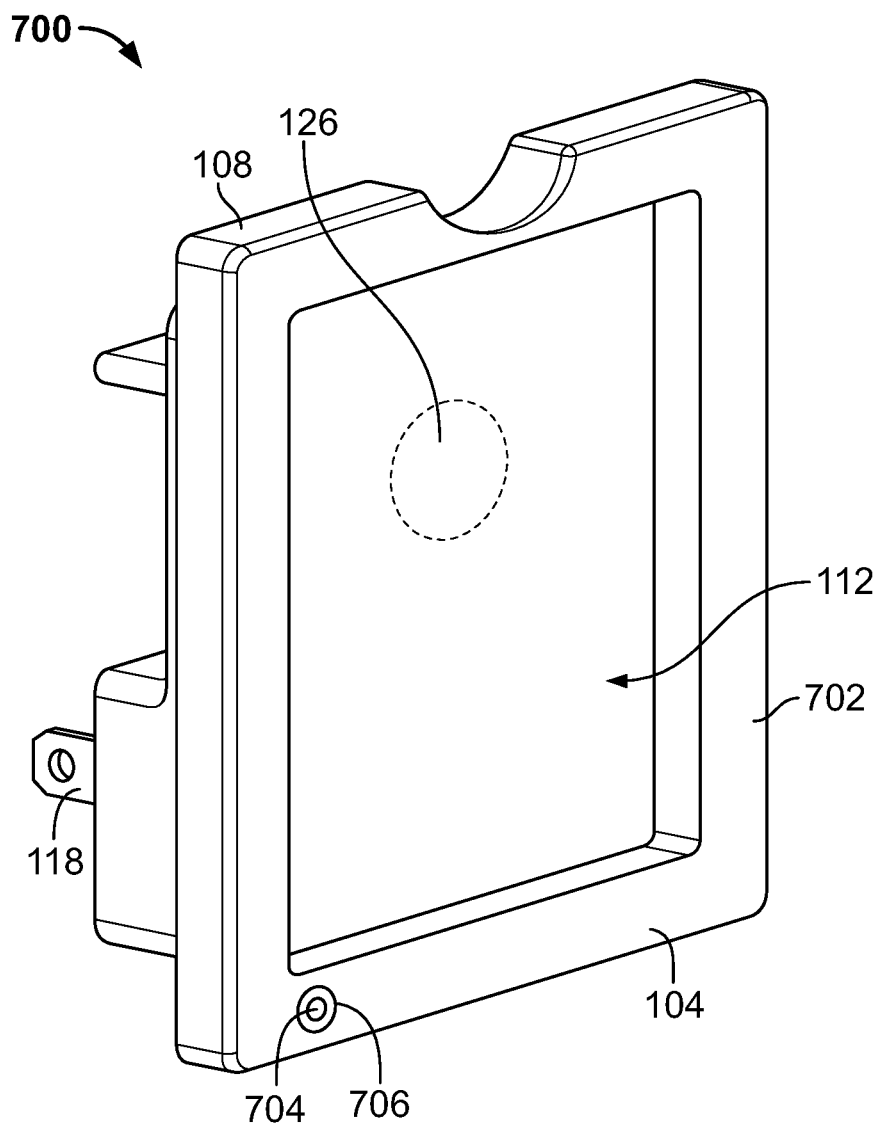
FIG. 27 is a still different embodiment of a dispensing device similar to the one shown in FIG. 1, further including a sensor for activation of the device.

Now referring to FIG. 27, an alternative embodiment of a dispensing device 700 is provided that is similar to the dispensing device 100 except for the below noted differences. The dispensing device 700 includes a frame 702 with a sensor 704 disposed within an orifice 706. While the sensor 704 and the orifice 706 of the present embodiment are disposed within a lower corner of the front face 104 of the frame 702, the sensor 704 and the orifice 706 may be located on any portion of the front face 104. In other embodiments, the sensor 704 and the orifice 706 are provided within the rear face 106, the sidewalls 108, or within the front or rear recesses 112, 114 of the frame 702. Different types of sensors may be used independently or in combination, including motion, light, and/or odor sensors. Other sensors may also be included as would be known to those of the skill in the art. The sensor 704 is preferably adapted to activate the heating element 125 in response to a sensed condition.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A volatile material container, comprising:
   a blister having a bottom wall, a peripheral flange, and a sidewall extending therebetween;
   a vapor permeable membrane attached to the peripheral flange and extending across the blister, wherein the vapor permeable membrane in conjunction with the bottom wall and the sidewall contain a volatile material within the blister; and
   a stationary magnetic element disposed entirely within the blister.

2. The volatile material container of claim 1, wherein the magnetic element is attached to the vapor permeable membrane.

3. The volatile material container of claim 1, wherein the magnetic element is attached to the bottom wall of the blister.

4. The volatile material container of claim 1, wherein the magnetic element is attached to the sidewall.

5. The volatile material container of claim 1, wherein a plurality of magnetic elements are disposed within the blister.

6. The volatile material container of claim 1, wherein the magnetic element is adapted to be attracted to a corresponding magnetic element in a dispensing device.

7. A volatile material container, comprising:
   a blister having a bottom wall, a peripheral flange, and a sidewall extending therebetween;
   a vapor permeable membrane attached to the peripheral flange and extending across the blister, wherein the vapor permeable membrane in conjunction with the bottom wall and the sidewall contain a volatile material within the blister; and
   a stationary magnetic element disposed between the blister and the vapor permeable membrane.

* * * * *